(12) United States Patent
Haslam et al.

(10) Patent No.: US 6,759,012 B2
(45) Date of Patent: Jul. 6, 2004

(54) PIN HOLDER FOR A MICROARRAYING APPARATUS

(75) Inventors: James Keith Haslam, Dorset (GB); John Richard Andrews, Dorset (GB)

(73) Assignee: Genetix Limited, Hampshire (GB)

(*) Notice: Subject to any disclaimer, the term of this patent is extended or adjusted under 35 U.S.C. 154(b) by 68 days.

(21) Appl. No.: 09/985,555

(22) Filed: Nov. 5, 2001

(65) Prior Publication Data

US 2003/0086827 A1 May 8, 2003

(51) Int. Cl.[7] ................................................. B01L 3/02
(52) U.S. Cl. ........................ 422/100; 422/99; 422/104; 436/180; 436/174; 101/93.04; 101/93.05; 211/60.1; 211/69.1; 400/124.01
(58) Field of Search ........................... 422/99, 100, 104; 436/180, 174; 101/93.04, 93.05; 346/140.1; 400/124.01, 124.14, 124.11, 124.28, 124.3; 211/60.1, 69.1, 69, 70.6; D24/227, 228, 229, 230, 231; 269/287; 223/109 R; 433/74

(56) References Cited

U.S. PATENT DOCUMENTS

| | | | |
|---|---|---|---|
| 1,541,672 A * 6/1925 | Tulay | .......................... | 206/199 |
| 2,488,535 A * 11/1949 | Hamburg | ..................... | 118/500 |
| 3,765,075 A * 10/1973 | Olney et al. | ..................... | 227/3 |
| 3,877,690 A * 4/1975 | Owens | .......................... | 269/265 |
| 5,296,082 A * 3/1994 | Kubo | .......................... | 156/500 |
| 5,756,050 A * 5/1998 | Ershow et al. | ............... | 422/100 |
| 5,882,930 A * 3/1999 | Baier | .......................... | 436/49 |
| 5,962,329 A * 10/1999 | Ershov et al. | ................. | 436/50 |
| 6,024,925 A * 2/2000 | Little et al. | ................... | 422/100 |
| 6,051,190 A * 4/2000 | Birch et al. | ................... | 422/100 |
| 6,086,825 A * 7/2000 | Sundberg et al. | ............ | 422/100 |
| 6,101,946 A * 8/2000 | Martinsky | ..................... | 101/494 |
| 6,197,261 B1 * 3/2001 | Linville et al. | .............. | 422/104 |
| 6,255,116 B1 * 7/2001 | Leber et al. | ................... | 436/54 |
| 6,255,119 B1 * 7/2001 | Baier | .......................... | 436/180 |
| 6,269,846 B1 * 8/2001 | Overbeck et al. | ............... | 141/1 |
| 6,360,663 B1 * 3/2002 | Gutfleisch | ..................... | 101/465 |
| 6,418,946 B1 * 7/2002 | Marinaro et al. | ........ | 134/166 R |
| 6,432,366 B2 * 8/2002 | Ruediger et al. | ............ | 422/129 |
| 6,497,155 B1 * 12/2002 | Feygin et al. | ............. | 73/863.22 |
| 6,551,557 B1 * 4/2003 | Rose et al. | .................. | 422/100 |
| 2001/0049149 A1 * 12/2001 | Kennedy et al. | ............. | 436/180 |
| 2002/0142483 A1 * 10/2002 | Yao et al. | .................... | 436/180 |
| 2002/0151077 A1 * 10/2002 | Schermer et al. | .............. | 436/43 |
| 2002/0176805 A1 * 11/2002 | Han-Oh et al. | .............. | 422/100 |
| 2003/0016982 A1 * 1/2003 | Horii et al. | ............ | 400/124.01 |
| 2003/0059344 A1 * 3/2003 | Brady et al. | ................. | 422/100 |

OTHER PUBLICATIONS

TeleChem International, Inc.; Microarray Hardware>Pin Racks.*
Standard Imaging; Vertical Needle Holder Ref 90073.*
SeeDos; Vertical Needle Holder.*
Majer Precision Engineering; Holders for DNA Array Pins.*
VP–Scientific; Pin Tool Accessories.*
MED–TEC; Needle boxes/cradles/holders.*
Standard Imaging; Needle Cradle Ref 90095.*
MED–TEC; Needle Cradle.*
TES Electrolysis; The On–line Electrolysis Superstore!*

* cited by examiner

*Primary Examiner*—Jill Warden
*Assistant Examiner*—Brian Gordon
(74) *Attorney, Agent, or Firm*—Foley & Lardner

(57) ABSTRACT

A pin holder for a microarraying apparatus comprising at least one group of bodies of circular cross-section packed together to form a network of pathways in gaps between the bodies; and an array of pins slidably arranged in the pathways. The pins are held in parallel to each other automatically as a result of the self organized packing of the circular cross-section bodies, which may be spheres, for example ball bearings, or cylindrical, for example needle roller bearings. The pin holder provides for very accurate parallel alignment of the pins, low pin friction, as well as low cost and complexity of manufacture.

15 Claims, 8 Drawing Sheets

US 6,759,012 B2

PIN HOLDER FOR A MICROARRAYING APPARATUS

BACKGROUND ART

The invention relates to an apparatus for and method of holding pins. More especially, but not exclusively, the invention relates to holding pins in a pin-head as widely used in the field of chemistry and biotechnology for microarraying and other applications.

Microarraying is a technique in widespread use. Conventional microarraying is based on standard multi-well plates having a 4.5 mm grid and 384 wells, although other sizes are available. Liquid samples are stored in the wells of a well plate. The liquid may be assays or any other biological or chemical sample of interest. Sub-samples of the liquid within the well plates are carried to and deposited on a spotting surface as required. Usually many such deposits are needed and microarraying is a process whereby multiple deposits can be made simultaneously and under machine automation.

FIG. 1A of the accompanying drawings shows schematically a bed of an exemplary microarraying apparatus 100. A number of well plates 110 are shown on the apparatus bed. The well plates 100 contain liquid to be spotted onto an array of microscope-type slides 120. The apparatus has a translatable head mechanism 130 which carries and positions the pin holder 140 in three orthogonal axes x, y and z.

FIG. 1B of the accompanying drawings shows schematically a more detailed view of a conventional pin holder 140 designed to carry a 6×4 rectangular array of pins 170. Each of the pins 170 is guided by an upper hole 180 and a lower hole 190 within the pin holder 140 so as to remain nominally vertical. The separation of neighboring holes matches that of the well plate spacing. The pins 170 are free to slide vertically within the pin holder 140 and a collar 175 provides an abutment for the pins 170 to define the bottom point of the pins 170.

In operation, the translatable head mechanism 130 is initially positioned so as to align the pins 170 with the required section of well plate 110. The pin holder 140 is then driven by the head mechanism 130 so as to partially immerse the pins 170 in the liquid to be spotted. Surface tension ensures that samples of fluid remain on the pins 170 as they are lifted away from the well plate. The pin holder 140 is then carried by the head mechanism 130 to the required location for spotting where it is again driven downwards to deposit some or all of the carried fluid at the chosen location. This can be achieved by bringing the pins 170 into direct contact with the surface 120. To avoid the necessity of precise vertical positioning of the pin holder 140 the pins 170 are free to slide vertically so as to limit the force applied to the spotting surface 120 as the pins 170 contact it. The head mechanism 130 may be lifted and re-positioned for further spotting with the fluid remaining on the pins 170, or it may be lifted and returned to the well plates 110 for re-coating with different fluid samples before further spotting. Typically, an extended and pre-programmed series of spotting operations will be undertaken automatically by the microarraying apparatus.

FIG. 2A of the accompanying drawings shows the resulting fluid deposition pattern that would occur from a single spotting operation with the pin holder 140 shown in FIG. 1B. There are 24 spots in a regular rectangular array and with a pitch which matches the well plate spacing. It is conventional to deposit a higher density of spots on the spotting surface 120 by repositioning the head 130 to a position slightly displaced from the initial spotting position for further spotting.

FIG. 2B of the accompanying drawings shows the resulting fluid deposition pattern that would occur from two further spotting operations, each slightly displaced from the previous.

FIG. 2C of the accompanying drawings shows the resulting fluid deposition pattern that would arise from many closely spaced spottings. Each of the individual boxes schematically represents a dense grid of spottings generated by a single pin. In order to reliably reproduce these dense grids, which typically comprise an 11×11 square grid of spots within the 4.5 mm pin separation, the pins 170 must be fixed such that their tips maintain the standard 4.5 mm spacing to a certain degree of accuracy, typically about 30 μm or better. The characteristic effect of a single misaligned pin in the spot pattern of FIG. 2C is shown as the uniformly displaced group of spots 230.

FIG. 3A and FIG. 3B of the accompanying drawings show, in grossly exaggerated form, two possible sources of pin misalignment error. FIG. 3A shows an example where the upper hole 180 and the lower hole 190 are not axially aligned. FIG. 3B shows an example where the upper hole 180 and the lower hole 190 are not co-parallel. These alignment errors require the guiding holes 180, 190 to be oversized to allow free movement of the pins. However, these oversized holes themselves can lead to spotting errors in cases where the holes 180, 190 are relatively well aligned such that a pin becomes free to move away from the vertical and rattle within the pin holder. This results in scatter about the otherwise regular spot pattern associated with the rastering of the affected pin.

The high-tolerance machining required to minimize the problems associated with misalignment of the holes in the pin holder leads to high manufacturing costs. Conventional drilling techniques are unable to provide the required accuracy and jig grinding is necessary. The cost of jig grinding each hole in a pin holder of the type described above is significant. With a pin holder containing 48 holes the machining cost of the pin holder makes up a significant proportion of the overall cost of the complete microarraying apparatus. It is therefore desirable to provide a pin holder which provides a high degree of accuracy for the pin guidance and which can be fabricated more cheaply and easily than a conventional pin holder.

SUMMARY OF THE INVENTION

According to a first aspect of the invention there is provided a pin holder for a microarraying apparatus comprising: at least one group of bodies of circular cross-section packed together to form a network of pathways in gaps between the bodies; and an array of pins slidably arranged in at least a subset of the pathways.

With the invention, the pins are held parallel to each other automatically as a result of the self organized packing of the circular cross-section bodies. This is a great improvement over the prior art approach described above in which guide holes for the pins are bored or ground individually, and thus inherently will not be parallel to each other and will also suffer from eccentricity errors in the case that the pins are guided in two or more vertically displaced guide holes.

With the invention, any misalignment of the circular cross-section bodies will be collective, so that all the pins will be misaligned in the same way and thus remain parallel to each other. Such a misalignment will therefore cause no net effect on the spotting process.

In one embodiment, the at least one group of bodies comprises a group of spherical bodies arranged in a common plane, such as ball bearings. More specifically, first and second groups of spherical bodies are preferably arranged in first and second planes vertically displaced from one another.

In another embodiment, the at least one group of bodies comprises a group of cylindrical bodies, such as needle roller bearings.

With the invention, the principal contributory factor to irregularity in the pin alignment, and thus spot spacing, will be irregularity in the size of the circular cross-section bodies. However, ball bearings (i.e. spheres) or needle roller bearings (i.e. cylinders) are manufactured to a very high degree of dimensional uniformity and are mass produced items of low cost. They are also available in a variety of materials, such as stainless steel, tungsten carbide and ceramic. A pin holder with a 4×6 pin array can be manufactured using conventional machining and by purchasing 70 ball bearings. This compares with having to jig grind the 48 holes needed for a conventional 4×6 pin holder, as described above. The invention thus not only provides a technically superior solution in terms of pin alignment accuracy, but does so in a way which reduces the cost of manufacture of the pin holder by two orders of magnitude. Indeed the cost reduction of the pin holder that is realizable with the invention can impact significantly on reducing the total cost of an entire microarrayer.

With the invention, the pin outer surfaces are located by point contacts (as considered in plan view) between the outer surfaces of nearest neighbor circular cross-section bodies, with the number of point contacts being defined by the number of nearest neighbor circular cross-section bodies. With a square packing, the number will be four and with a hexagonal close packing, the number will be three. The point contacting of the pins within their guides greatly reduces friction of the pins, in comparison with the prior art approach of using circular cross-section guide holes in which a full circumferential portion of the pin's outer surface is in contact with the whole inner surface of the guide holes.

If the circular cross-section bodies are spheres, then the contacting between the pins and guides will truly be point contacting. If two layers of spherical bodies are used, there will thus be eight points of contact in total for each pin. The use of spheres is considered to be the best mode of the invention, since any dirt or foreign bodies that find their way to the pin holder pathways will be self-cleaned away from the contact surfaces, and therefore not compromise pin alignment and motion. Alternatively, if the circular cross-section bodies are cylindrical, then the contacting between pins and guides will be line contacts. These will also be self-cleaning, but not to the same extent as with spherical bodies. Moreover, friction of the pins in the pathways will be larger than for spherical bodies.

The bodies are preferably packed together in a square grid. To provide a 4×6 pin array, which is a standard, the square grid of bodies is preferably configured to provide a network of 4×6 pathways, also conformant to a square grid. This can be done most efficiently when the square grid of bodies consists of a 5×7 arrangement of bodies, also conformant to a square grid.

The standard spacing for microarraying is 4.5 mm. To design the pin holder to conform to this standard, the circular cross-section of the bodies preferably has a diameter of 4.5±0.02 mm, 4.5±0.01 mm, 4.5±0.005 mm or 4.5±0.0025 mm. A variance in the diameters of the bodies is preferably less than ±0.0025 mm, i.e ±2.5 $\mu$m. With bodies of 4.5 mm diameter, the circular cross-section of the pins should nominally have a diameter of 1.864 mm from purely trigonometric considerations. However, to provide sufficient clearance for a smooth fit, the actual diameter should be somewhat less, namely 1.860±0.02 mm, 1.860±0.01 mm or 1.860±0.004 mm. A desired diameter variance between pins of a certain specified diameter is ±0.004 mm, i.e ±4 $\mu$m.

Accordingly, in a second aspect of the invention there is provided a set of pins for a pin holder of a microarraying apparatus, wherein each pin comprises a shank of circular section leading to a tip for carrying and dispensing liquid, wherein the shank has a diameter of 1.860±0.02 mm, 1.860±0.01 mm or 1.860±0.004 mm, for example.

Other pin arrangements may also be used. For example, the pins may be arranged in a triangular or rectangular array, instead of a square array. This is possible by packing the bodies into a hexagonal close packed array, instead of square grid. Moreover, with a square grid of bodies, rectangular pin arrays can be provided by utilizing only a subgroup of the pathways.

According to a third aspect of the invention there is provided a spotting method comprising:
(a) providing a spotting head with a pin holder comprising at least one group of bodies having circular cross-section packed together to form a regular network of pathways in gaps between the bodies;
(b) providing an array of pins slidably arranged in at least a subset of the pathways; and
(c) selectively driving the pins in the pathways to deposit liquid on a spotting surface.

Further aspects of the invention relate to a microarraying apparatus and a head for a microarraying apparatus comprising a pin holder according to the first aspect of the invention.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 4A:
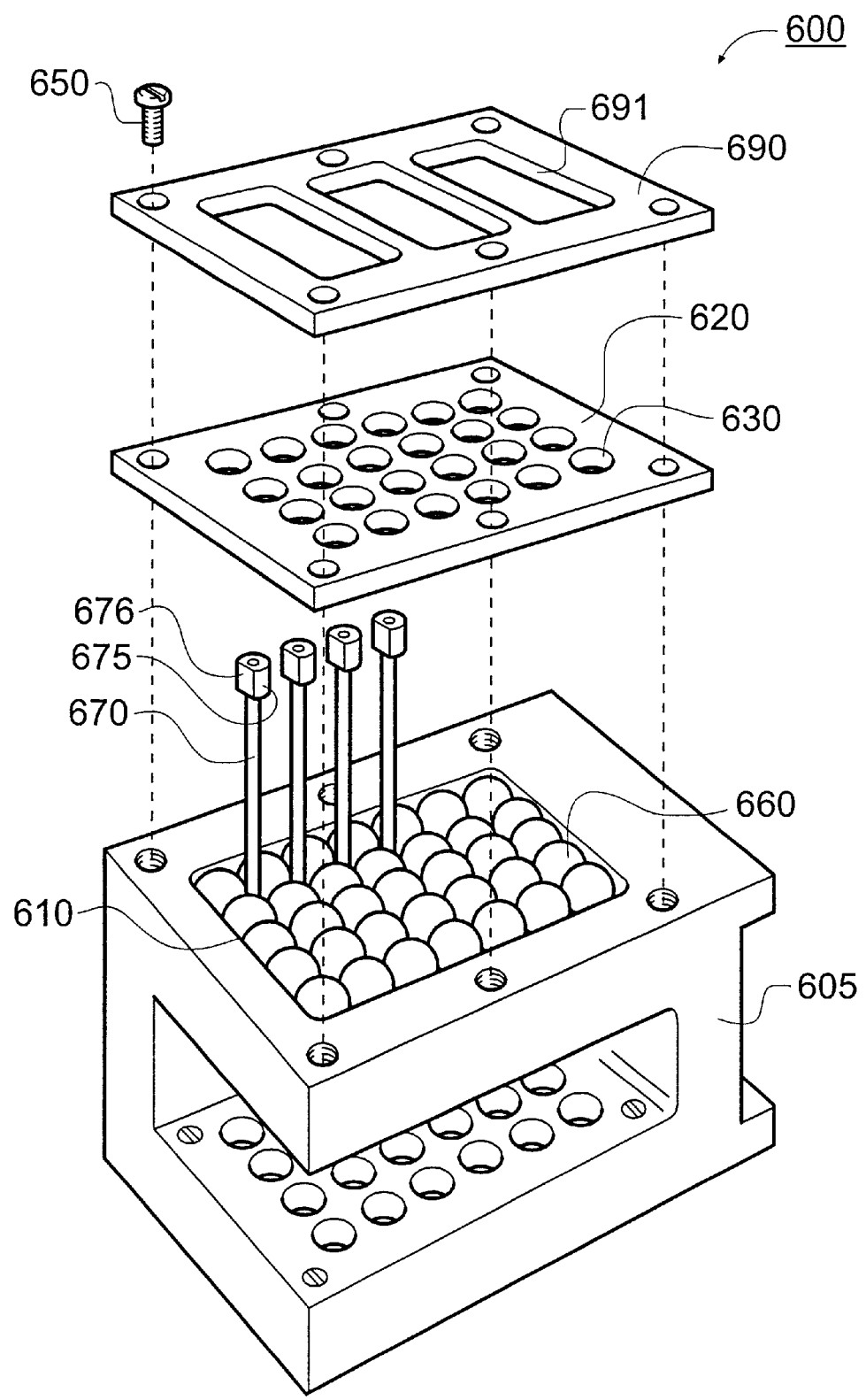
FIG. 4A is a schematic perspective view of a pin holder according to an embodiment of the invention.

FIG. 4A is a schematic drawing of a pin holder 600 for a microarraying apparatus according to one embodiment of the invention. The pin holder 600 comprises a main body 605 holding a first planar array 660 and a second planar array (not shown) of 35 spherical bodies which are held in planes vertically displaced from one another. The spherical bodies 660 may preferentially be steel ball bearings. A recess 610 in the main body 605 comprises four inner side walls in a rectangular arrangement and a perforated lower surface. The recess is sized so as to confine the upper array of balls 660 to a 5×7 square grid, thus providing a network of 4×6 pathways in gaps between the balls 660 which is also conformant to a square grid. A cover plate 620, containing holes 630 which align with the pathways between the balls, is attached to further constrain the balls. The perforations in the lower surface of the recess 610 are also aligned with the pathways between the balls. The inner walls of the recess 610 are rigid in the present embodiment. Alternatively, one or more of the inner walls may be deformable so as to provide an inwardly biasing force to maintain the packing. This could be advantageous where there is differential expansion between the recess 610 and the balls 660, for example. The lower array of balls is held in a similar fashion to the upper array of balls and is shown as a completed assembly in FIG. 4A. A 4×6 array of 24 pins 670 (of which four are shown) is slidably arranged within the network of pathways between the balls. Each pin has an abutment collar 670 and an anti-rotation flat 676, these will be described in more detail below. An anti-rotation guide plate 690 for the pins 670 is included and this will also be further described below. The overall assembly is held together by fasteners 650.

Figure 4B:
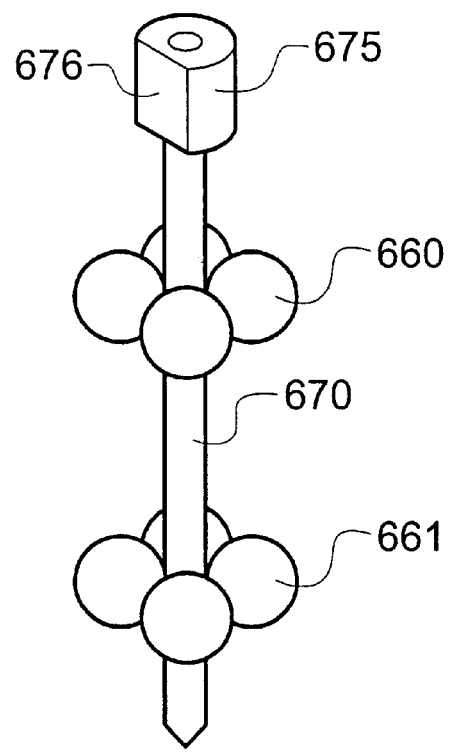
FIG. 4B is a schematic perspective view detailing the containment of one pin in the embodiment of FIG. 4A.

FIG. 4B is a schematic drawing which shows the guidance of an individual pin 670. A square group of four balls from the upper ball array 660 and the correspondingly aligned group from the lower ball array 661 are shown. The pin shank passes through the gaps defined by the balls of the upper and lower arrays 660,661 and is accordingly constrained to nominally vertical motion in a defined pathway.

Figure 4C:
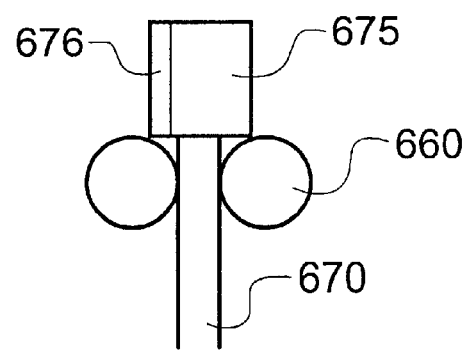
FIG. 4C is a schematic vertical section detailing the pin stop mechanism in the embodiment of FIG. 4A.

FIG. 4C is a schematic drawing which further details the holding of the upper portion of an individual pin 670. In operation the lowest point of travel of the pin is in the position shown in which its relative height is set by the contact of the base of the pin collar 675 with the upper ball array 660. The lengths of the pins 670 are the same to provide a common horizontal plane of pin tips suitably spaced below the main body 605 when the pins are at their bottom position, as illustrated in FIG. 4C. The pins 670 are free to slide within the pin holder 600, under positive actuation or to account for any over-travel onto a spotting surface, for example.

Figure 4D:
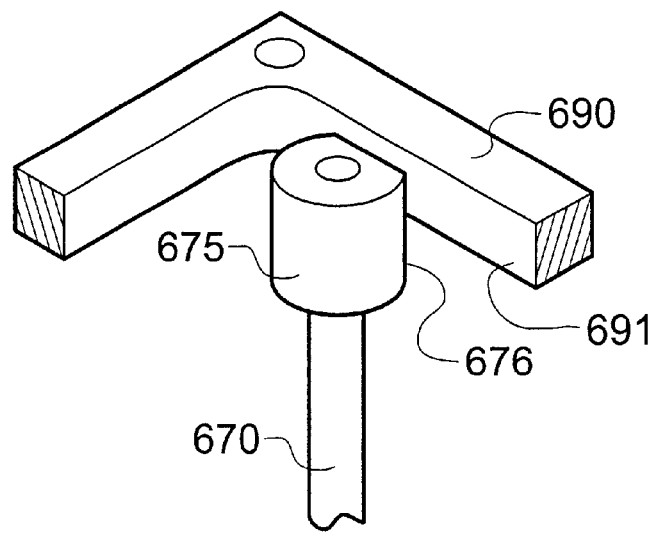
FIG. 4D is a schematic perspective view detailing the pin anti-rotation mechanism in the embodiment of FIG. 4A.

FIG. 4D is a schematic drawing which shows an expanded upper portion of one of the pins 670 and a section of the anti-rotation guide plate 690. The anti-rotation guide plate 690 provides a facing surface 691 which is positioned so as to meet the anti-rotation flat 676 on the pin collar 675, and thus limit the rotation of the pin 670. The pin 670 remains free to slide vertically. In this embodiment, the anti-rotation guide plate 690 contains six extended surfaces 691 which are defined by pairs of opposing inner faces of three openings within the guide plate 690. Each of these surfaces 691 provides a facing surface for the flats 676 of a set of four pins 670 arranged in a given pin column.

Figure 5:
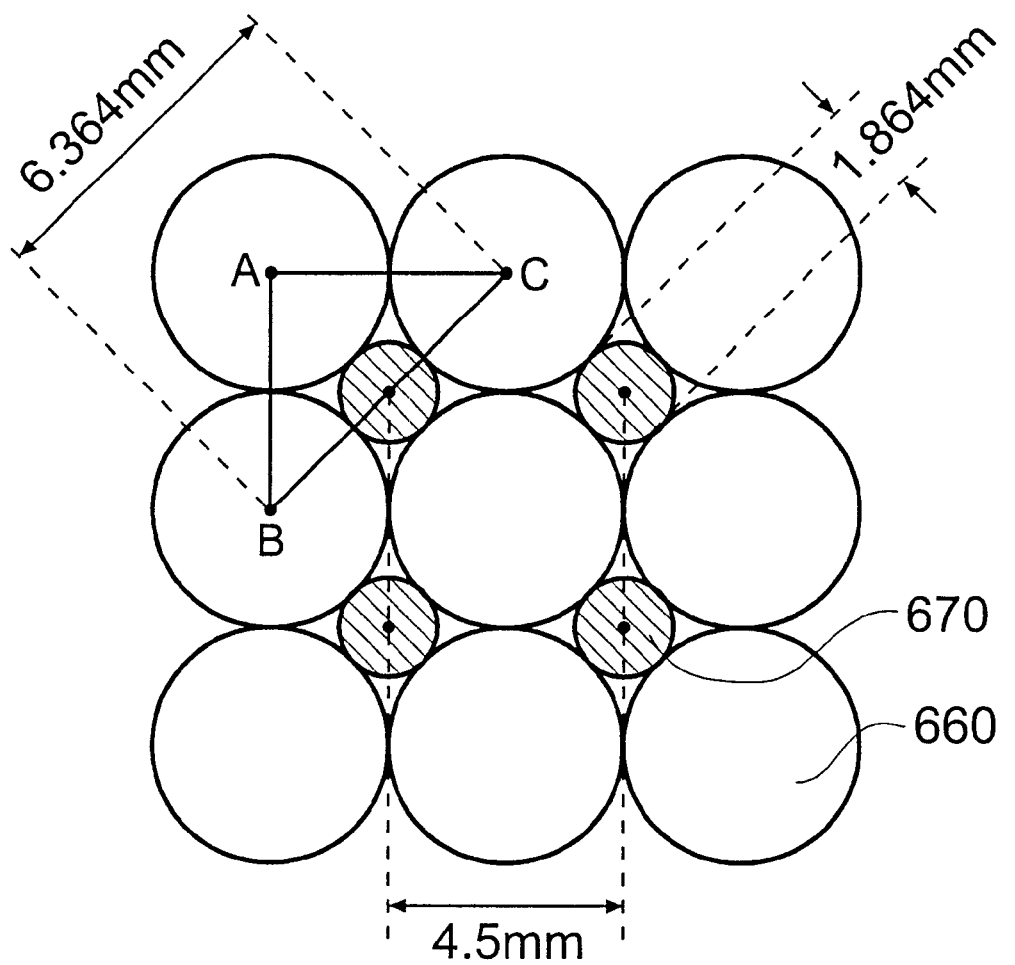
FIG. 5 is a schematic horizontal section view detailing a section of a ball array in the embodiment of FIG. 4A.

FIG. 5 is a schematic drawing in plan view which shows a group of balls 660 and pins 670 of a particularly preferred set of cross-sectional dimensions. The diameters of the balls 660 and the pins 670 are 4.5 mm and 1.864 mm respectively. These sizes provide pins 670 which are closely matched to the gaps through which they pass, and pin spacings which conform to the current industry standard spacing for microarraying which is 4.5 mm. By using a square array of spherical balls of diameter 4.5 mm, the required 4.5 mm pin spacing is achieved. With reference to FIG. 5, a ball diameter of 4.5 mm provides distances $\overline{AB}$ and $\overline{AC}$ between the centers of touching-neighbor balls of 4.5 mm and a corresponding distance $\overline{BC}$ between the centers of diagonal-neighbor balls of ($\sqrt{2}\times4.5$) mm, which is 6.364 mm (to four significant figures). A preferred pin diameter is that which closely matches the gaps between the balls and is (($\sqrt{2}-1)\times4.5$) mm. This is 1.864 mm (to four significant figures). The precision to which these prescribed sizes are met will determine both the accuracy to which the 4.5 mm pin spacing is maintained, and how strictly the pins 670 are constrained to vertical motion. Suppose the pins 670 are of length l and the upper and lower arrays of balls 660,661 are separated by a distance d. A translational error in the intersection of a pin's longitudinal central axis with the plane defined by one of the ball arrays of magnitude δx will result in a translational error of approximately (l/d×δx) in the position of the pin's tip. This indicates that it is advantageous for the pins 670 not to descend unnecessarily far below the lower ball array 661. The error in pin tip position may be due to either a positional deviation in the centroid of a gap or an undersized pin tilting away from the vertical. In either case the required fractional mechanical precision of the ball and pin diameters must be better by at least a factor of around (l/d) than the required final fractional precision of the pin tip positions. For example, to satisfy the minimum level of accuracy for spotting described above, the diameters of the balls 660, 661 and pins 670 should be accurate to at least 10 μm, preferably 5 μm. However, a higher level of precision may be advantageous.

There are several advantages of this particular embodiment. The choice of spherical balls 660,661 provides the pins 670 with only eight points of contact, as opposed to the cylindrical surface contact areas between the pins and holes within the prior art described above. This allows the pins 670 to slide more freely within the pin holder 600, reducing both the likelihood of sticking, and the force applied to the spotting surface during the over-travel of the pin holder 600. The points of contact are also naturally self cleaning under the action of the vertical motion of the pins 670. This reduces the risk of debris forming in the pathway and compromising the alignment or slidable motion of the pins 670. Furthermore, steel balls of the type commonly used within bearing mechanisms are readily available in a variety of accurate sizes. Balls can also be easily made from a variety of metals, ceramics and plastics which might be especially well suited to particular embodiments of the invention.

Figure 6A:
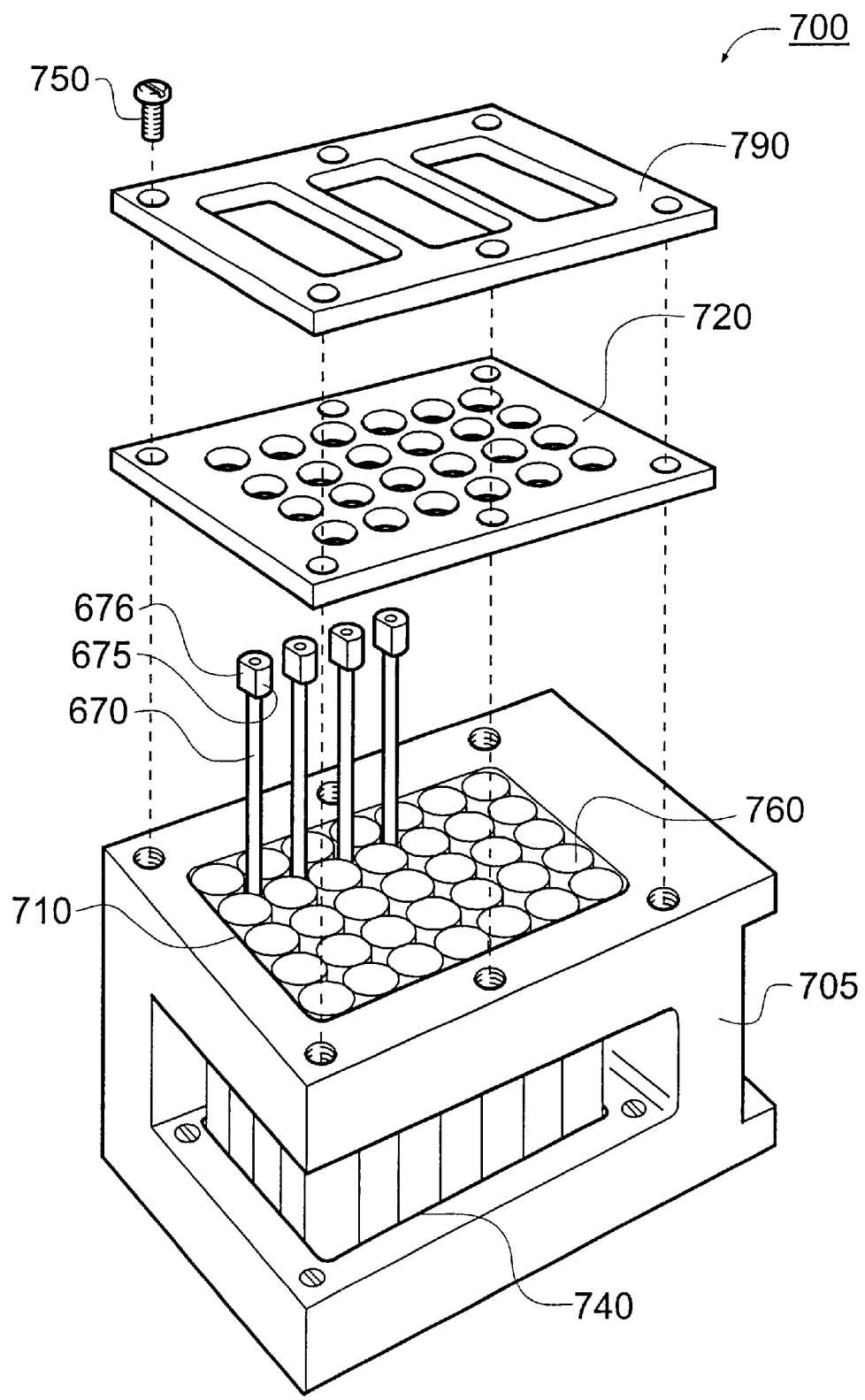
FIG. 6A is a schematic perspective view of a pin holder according to another embodiment of the invention.

FIG. 6A is a schematic drawing of a pin holder 700 for a microarraying apparatus according to another embodiment of the invention. The pin holder 700 comprises a main body 705 holding a planar array of 35 cylindrical bodies 760. The cylindrical bodies 760 may preferentially be sections of steel rod or needle roller bearings. These bodies may have rounded ends, although flat ends are shown for ease of representation. A recess 740 in the lower portion of the main body 705 comprises four inner side walls in a rectangular arrangement and a perforated lower surface. The recess supports the rods 760 and confines them to a 5×7 square grid, thus providing a network of 4×6 pathways in gaps between the rods 760 which is also conformant to a square grid. The perforations in the lower surface of the recess 740 are aligned with the pathways between the rods 760. The inner walls of the recess are rigid in the present embodiment. Alternatively, one or more walls may be deformable as will be understood from the description of the previous embodiment. The rods are optionally further constrained by an enclosure 710. The enclosure 710 provides inner side walls which constrain the rods 760 in the same way as the inner side walls of the recess 740. An array of 24 pins 670 (of which four are shown) are slidably arranged within the network of pathways between the rods 760. The pins are as described in the previous embodiment of the invention. The pin holder 700 further comprises a cover plate 720, an anti-rotation guide plate 790 for the pins 670, and fixings 750. These items will be understood from the description of the corresponding items made in connection with the first embodiment and shown in FIG. 4A.

Figure 6B:
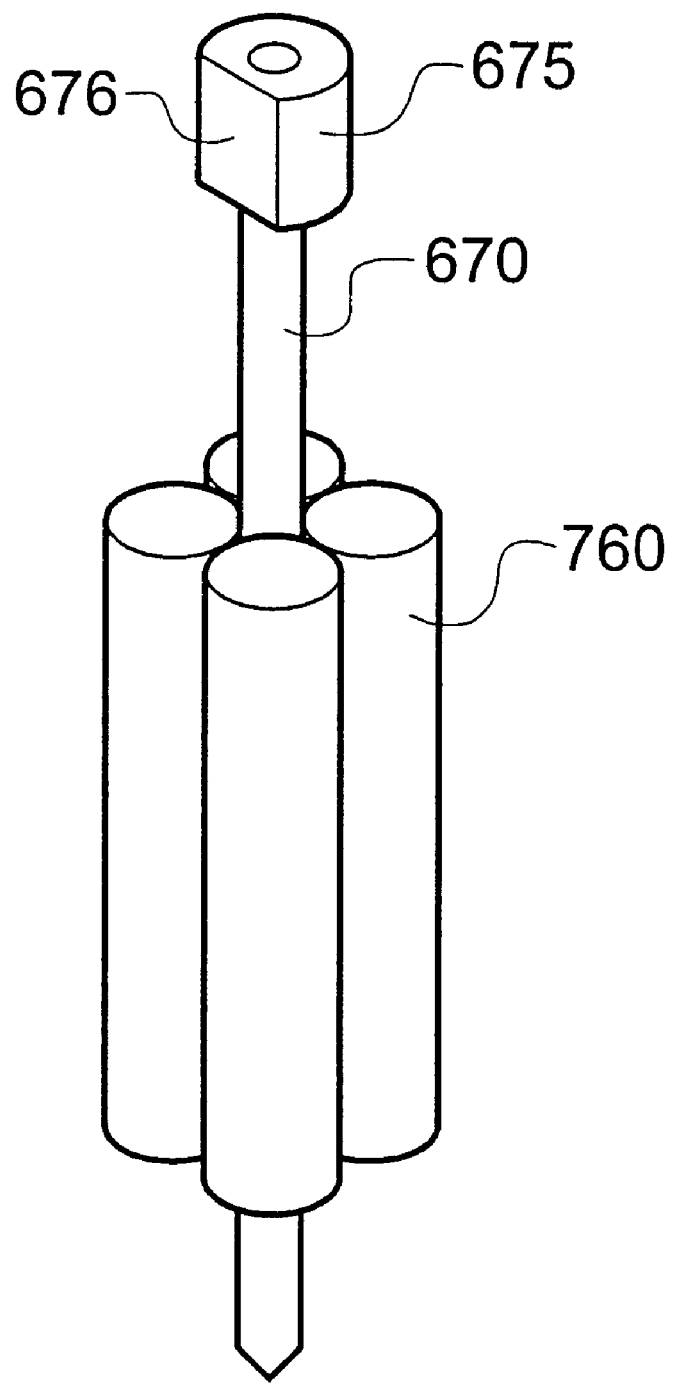
FIG. 6B is a schematic perspective view detailing the containment of a single pin in the embodiment of FIG. 6A.

FIG. 6B is a schematic drawing which shows the guidance of an individual pin 670 within this embodiment of the invention. A square group of four rods from the array 760 is shown. The pin shank passes through the gaps defined by the rods 760 and is accordingly constrained to nominally vertical motion.

Whilst the network of pathways in this embodiment of the invention is created in a different fashion to that of the previous embodiment, it is envisaged that other aspects of this embodiment, such as the carrying, positioning, rotation limiting and geometry of the pins, will be substantially similar to those aspects as described in the first embodiment.

It is recognized that different packing methods may be employed in embodiments of the invention which are otherwise similar to those outlined above. In particular, with a close hexagonal packing of bodies having circular cross-section an array of pins can be slidably arranged in a subset of the resultant pathways to provide different pin spacings.

Figure 7:
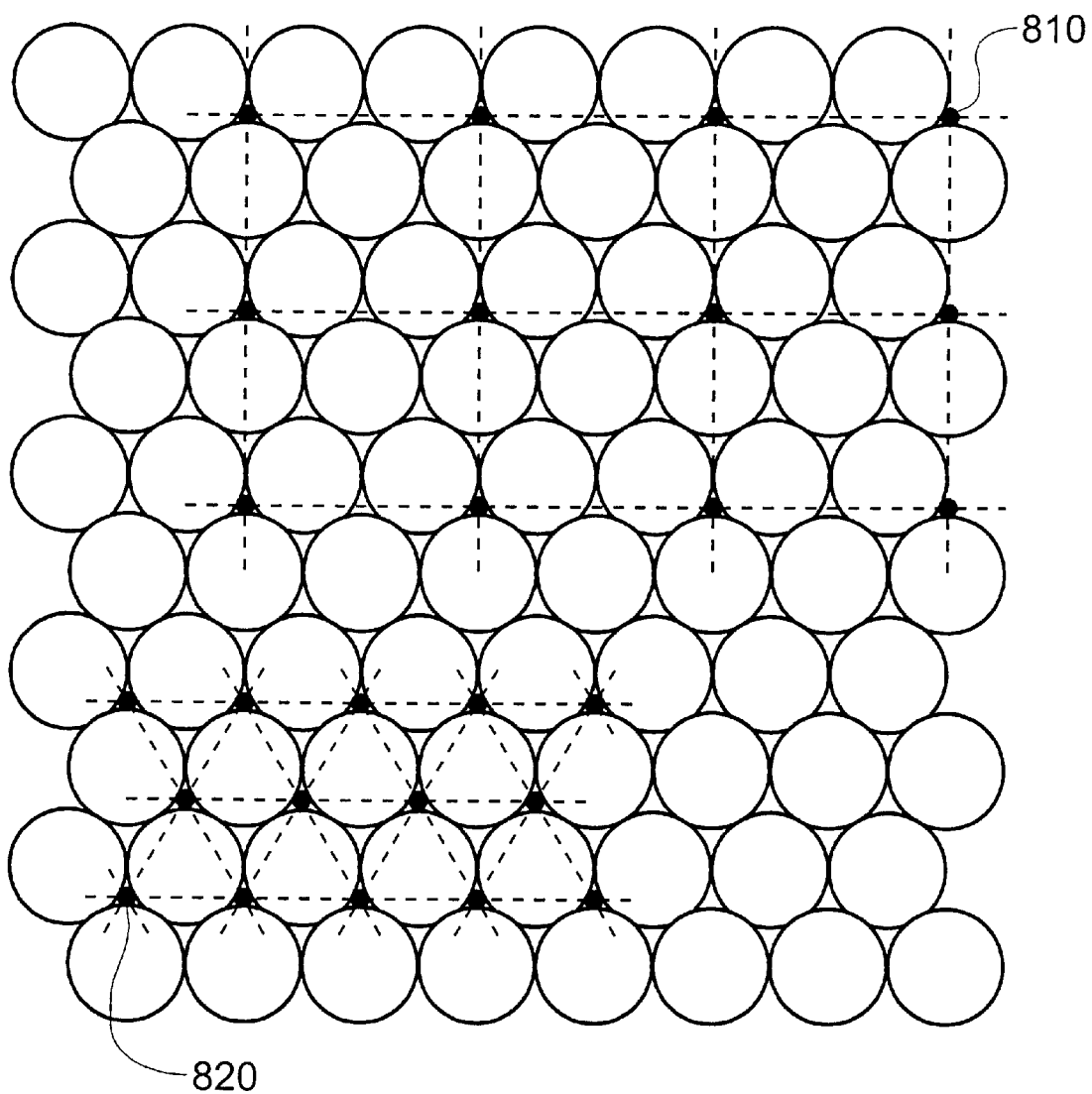
FIG. 7 is a schematic horizontal section view detailing a portion of a hexagonally close packed ball array according to another embodiment of the invention.

FIG. 7 is a schematic drawing showing a section of a planar array of hexagonally close packed bodies of circular cross-section according to further alternative embodiments, wherein the bodies may be spheres or cylinders. Two particular sub-arrays of gaps between the bodies, a rectangular grid 810 and a triangular grid 820, are indicated. Similar grids of different scale and/or aspect ratio are also provided for by this packing arrangement. As in the previous embodiments the sizes of the packing bodies and pins may have preferential and related sizes.

Figure 1A:
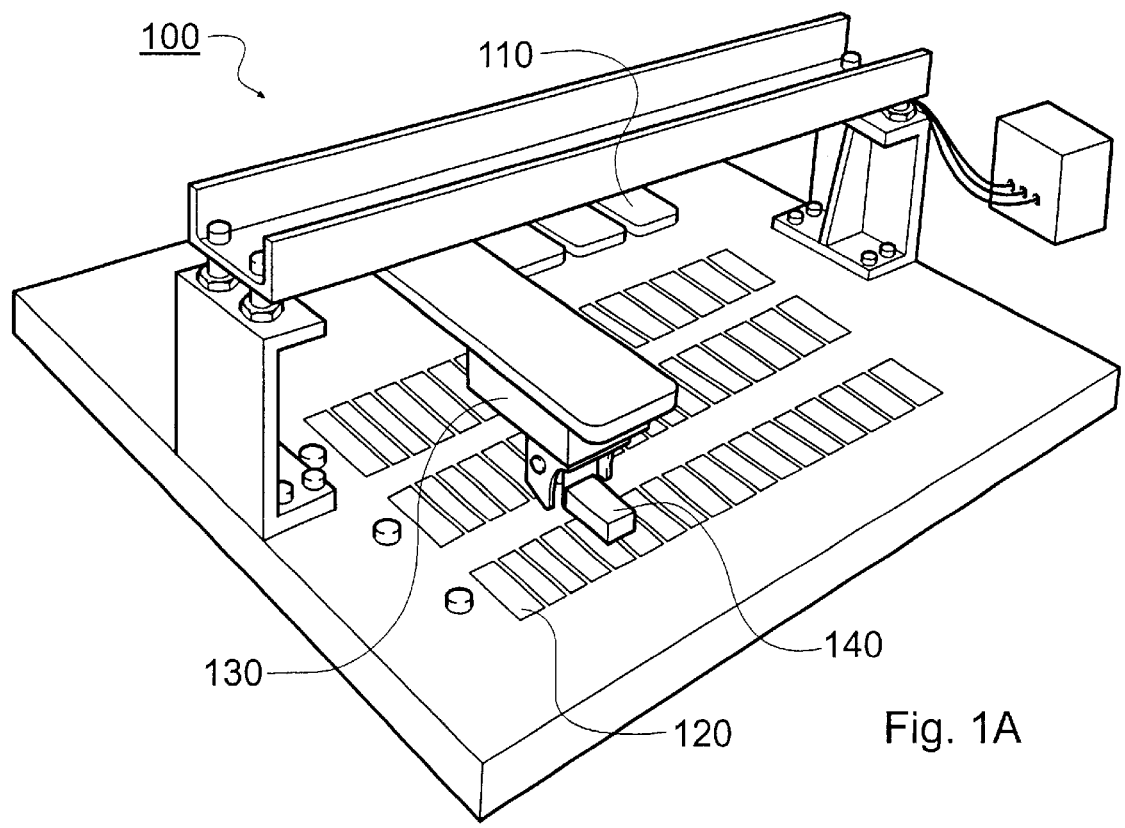
FIG. 1A is a schematic perspective view of a microarraying apparatus.
Figure 1B:
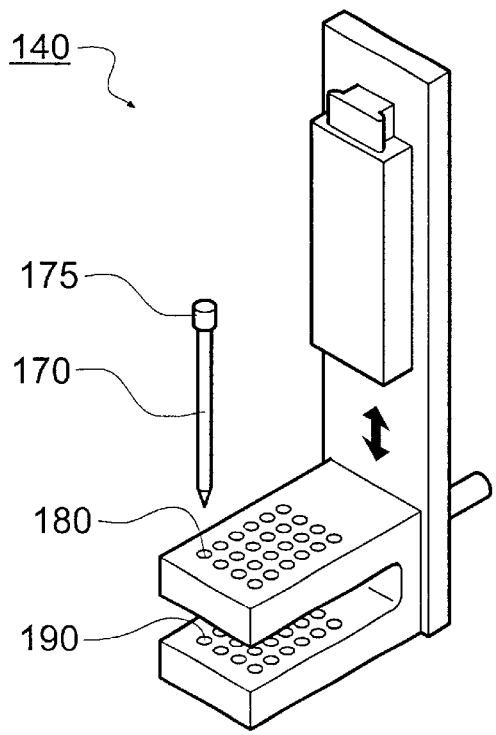
FIG. 1B is a schematic perspective view of a prior art pin holder for the microarraying apparatus of FIG. 1A.
Figure 2A:
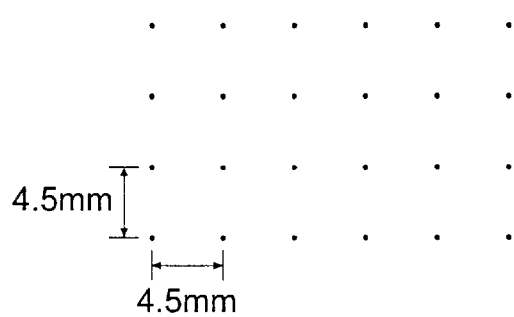
FIG. 2A is a schematic plan view of the spotting pattern associated with a single fluid deposition operation with an industry standard 6×4 square grid of pins.
Figure 2B:
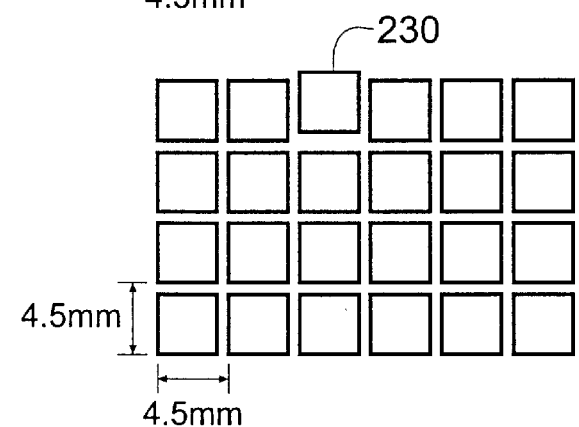
FIG. 2B is a schematic plan view of the spotting pattern associated with three closely spaced fluid deposition operations with a 6×4 square grid of pins.
Figure 2C:
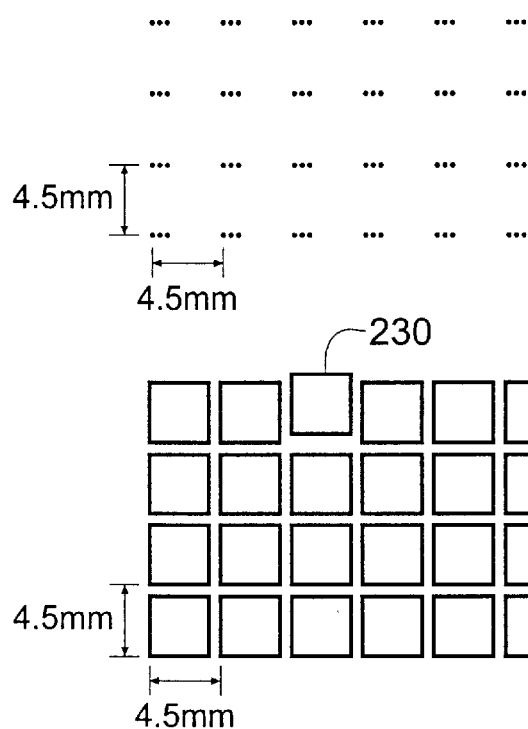
FIG. 2C is a schematic plan view of the spotting pattern associated with a rastered 11×11 square grid of closely spaced fluid deposition operations with a 6×4 square grid of pins.
Figure 3A:
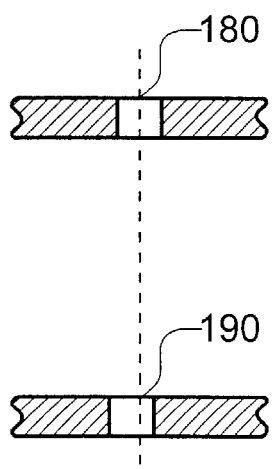
FIG. 3A is a schematic section of a prior art pin holder with upper and lower guide holes which are not co-axial.
Figure 3B:
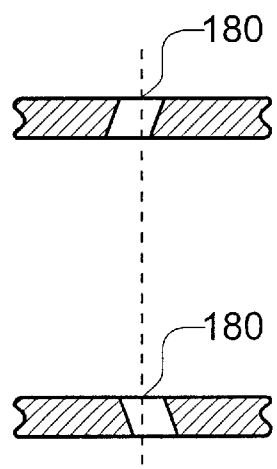
FIG. 3B is a schematic section of a prior art pin holder with upper and lower guide holes which are not co-parallel.

It will be understood that a pin holder embodying the invention may be fitted to a conventional microarrayer as part of the head 130, as illustrated in FIG. 1A for example, either as a retrofitting option, or with a newly manufactured microarrayer.

It is further envisaged that a method of spotting with a microarraying apparatus would comprise:
(a) providing a spotting head with a pin holder comprising at least one group of bodies having circular cross-section packed together to form a regular network of pathways in gaps between the bodies;
(b) providing an array of pins slidably arranged in at least a subset of the pathways; and
(c) selectively driving the pins in the pathways to deposit liquid on a spotting surface.

What is claimed is:

1. A pin holder for a microarraying apparatus comprising:
at least one group of bodies of circular cross-section packed together in a planar array to form a network of pathways in gaps between the bodies; and
an array of pins slidably arranged in at least a subset of the pathways.

2. A pin holder according to claim 1, wherein the at least one group of bodies comprises a group of cylindrical bodies.

3. A pin holder according to claim 1, wherein the at least one group of bodies comprises a group of spherical bodies arranged in a common plane.

4. A pin holder according to claim 1, wherein the at least one group of bodies comprises first and second groups of spherical bodies arranged in first and second planes vertically displaced from one another.

5. A pin holder according to claim 1, wherein the bodies are packed together in a square grid.

6. A pin holder according to claim 5, wherein the square grid of bodies provide a network of 4×6 pathways, also conformant to a square grid.

7. A pin holder according to claim 5, wherein the square grid of bodies consists of a 5×7 arrangement of bodies that provide a network of 4×6 pathways, also conformant to a square grid.

8. A pin holder according to claim 5, wherein the circular cross-section of the bodies has a diameter of at least one of 4.5±0.02 mm, 4.5±0.01 mm, 4.5±0.005 mm and 4.5±0.0025 mm.

9. A pin holder according to claim 8, wherein the circular cross-section of the pins has a diameter of at least one of 1.860±0.02 mm, 1.860±0.01 mm, and 1.860±0.004 mm.

10. A pin holder according to claim 1, wherein the at least one group of bodies forms a network of at least 4×6 pathways conformant to a square or rectangular grid.

11. A head for a microarraying apparatus comprising a pin holder according to claim 1.

12. A microarraying apparatus comprising a head according to claim 11.

13. A set of pins for the pin holder of claim 1 of the microarraying apparatus, wherein each pin comprises a shank of circular cross-section leading to a tip for carrying and dispensing liquid, wherein the shank has a diameter of at least one of 1.860±0.02 mm, 1.860+0.01 mm, and 1860+0.004 mm.

14. A spotting method comprising:
(a) providing a spotting head with a pin holder comprising at least one group of bodies having circular cross-section packed together to form a regular network of pathways in gaps between the bodies;
(b) providing an array of pins slidably arranged in at least a subset of the pathways; and
(c) selectively driving the pins in the pathways to deposit liquid on a spotting surface.

15. A spotting method comprising:
(a) providing a spotting head with a pin holder comprising at least one group of bodies having circular cross-section packed together in a planar array to form a regular network of pathways in gaps between the bodies;
(b) providing an array of pins slidably arranged in at least a subset of the pathways; and
(c) selectively driving the pins in the pathways to deposit liquid on a spotting surface.

* * * * *